United States Patent
Kasukawa et al.

[11] Patent Number: 6,046,233
[45] Date of Patent: Apr. 4, 2000

[54] AGENT FOR TREATING COR PULMONALE

[75] Inventors: Reiji Kasukawa; Masayuki Miyata, both of Fukushima; Yuji Ueno; Hiroshi Koike, both of Shizuoka; Hajimu Kurumatani; Shintaro Nishio, both of Kanagawa, all of Japan

[73] Assignee: Toray Industries, Inc., Chiba, Japan

[21] Appl. No.: 08/732,231

[22] PCT Filed: Feb. 27, 1996

[86] PCT No.: PCT/JP96/00443

§ 371 Date: Jan. 3, 1997

§ 102(e) Date: Jan. 3, 1997

[87] PCT Pub. No.: WO96/26721

PCT Pub. Date: Sep. 6, 1996

[30] Foreign Application Priority Data

Feb. 27, 1995 [JP] Japan ................................. 7-038169

[51] Int. Cl.⁷ ............................ A01N 43/08; A61K 31/34
[52] U.S. Cl. .................... 514/468; 514/461; 549/456; 549/458
[58] Field of Search ..................... 514/468, 461

[56] References Cited

U.S. PATENT DOCUMENTS

| | | | |
|---|---|---|---|
| 4,474,802 | 10/1984 | Ohno et al. .................. | 424/285 |
| 5,028,628 | 7/1991 | Tadepalli et al. ............. | 514/573 |
| 5,153,222 | 10/1992 | Tadepalli et al. ............. | 514/571 |
| 5,403,867 | 4/1995 | Okumura et al. .............. | 514/573 |
| 5,496,850 | 3/1996 | Mutoh et al. ................ | 514/468 |
| 5,508,303 | 4/1996 | Isogaya et al. .............. | 514/468 |

OTHER PUBLICATIONS

Yuki et al., "Orally administered beraprost sodium inhibits pulmonary hypertension induced by monocrotaline in rats", Tohoku J. Exp. Med. 173(4), pp. 371–5, 1994, see abstract.

Stedman's Medical Dictionary, 24th Edition, pp. 319 and 677, 1983.

*Primary Examiner*—Kevin E. Weddington
*Assistant Examiner*—Dwayne C. Jones
*Attorney, Agent, or Firm*—Birch, Stewart, Kolasch & Birch, LLP

[57] ABSTRACT

The present invention relates to an agent for treating cor pulmonale containing as an active ingredient a prostaglandin $I_2$ derivative represented by the following formula, or a pharmacologically acceptable salt thereof. The agent exhibits excellent effects in oral or parenteral administration.

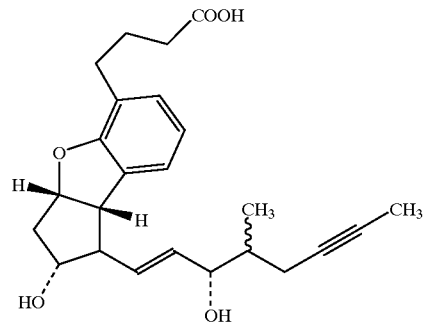

4 Claims, No Drawings

AGENT FOR TREATING COR PULMONALE

This application is a National Stage filing under 37 U.S.C. § 371 of PCT/JP96/00443, filed Feb. 27, 1996.

TECHNICAL FIELD

The present invention relates to an agent for treating cor pulmonale comprising a prostaglandin $I_2$ derivative such as, for example, beraprost, or a salt thereof as an active ingredient.

BACKGROUND ART

Cor pulmonale develops a disease condition in which an increase in the pulmonary vascular resistance due to an organic or functional abnormality of the lungs causes right ventricular pressure overload, resulting in right ventricular hypertrophy and further right ventricular insufficiency. Cor pulmonale is caused by various diseases, the critical mechanism of ventricular hypertrophy is not clarified, and no curative means is established. Although cor pulmonale is treated by causal disease treatment (including oxygen therapy) or using a diuretic and cardiotonic, an effective curative means has not yet been established.

On the other hand, prostaglandin $I_2$ ($PGI_2$, prostacyclin) which is known as a substance having the strong actions of inhibiting platelet aggregation and dilating the peripheral vessel (refer to "Nature" Vol. 268, p688, 1976) has an unstable exoenol structure, and thus $PGI_2$ is very unstable in a neutral aqueous solution and is converted into 6-oxo $PGF_1$ α which has substantially no physiological activity. This instability of $PGI_2$ brings about an important problem in utilizing this compound as a medicine. The $PGI_2$ is also unstable in vivo and thus has the fault that its physiological action has no persistency. Japanese Examined Patent Publication No. 1-53672 discloses, as compounds in which the faults of $PGI_2$ are significantly improved, $PGI_2$ derivatives having a skeleton in which the structure of the exoenol ether portion, that is a characteristic structure of $PGI_2$, is converted into an inter-m-phenylene type. However, this publication does not suggest the curative effects of those derivatives on cor pulmonale, and it has not yet been known that the $PGI_2$ derivatives have the curative effects on cor pulmonale.

As a result of extensive research for developing an agent for treating cor pulmonale having excellent efficacy and practicability, the inventors found that the compounds used in the present invention have the significant effect of ameliorating the condition of cor pulmonale, resulting in the achievement of the present invention.

DISCLOSURE OF THE INVENTION

The present invention provides an agent for treating cor pulmonale comprising as an active ingredient a 5,6,7-trinor-4,8-inter-m-phenylene prostaglandin $I_2$ derivative or a pharmacologically acceptable salt thereof represented by the following formula (I):

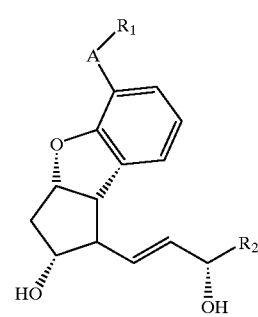

wherein $R_1$ is hydrogen, a carboxyl group or a functional derivative thereof, —$CH_2OH$, or a pharmacologically acceptable cation;

A is (1) —$(CH_2)_n$—, (2) —$(CH_2)_m$—CH=CH—$(CH_2)_p$—, (3) —$(CH)_m$—C≡C—$(CH_2)$p— or (4) —$CH_2$—O—$CH_2$— (wherein n is an integer of 0 to 3, and each of m and p is 0 or 1):

$R_2$ is (1) a straight chain or branched alkyl group having 5 to 10 carbon atoms, (2) —Ct H2t—$OR_3$ (wherein t indicates an integer of 1 to 5, and $R_3$ indicates a straight chain or branched alkyl group having 1 to 5 carbon atoms, or a phenyl group), (3) —Ct H2t—CH=C ($R_4$) ($R_5$) (wherein t indicates the same as defined above, and $R_4$ and $R_5$ each indicate hydrogen, a methyl group, an ethyl group, a propyl group or a butyl group); or (4) —Ct H2t—C≡C—$R_6$ (wherein t indicates the same as defined above, and $R_6$ indicates hydrogen, a methyl group or an ethyl group), and formula (I) indicates d-, l- and dl-forms.

BEST MODE FOR CARRYING OUT THE INVENTION

The inventors of this invention have already found prostaglandin $I_2$ derivatives are effective as an antiulcer agent, an anti-thrombogenic agent, an antihypertensive agent, and an antiasthmatic agent (Japanese Examined Patent Publication No. 1-53672).

However, this publication does not suggest that these derivatives have the curative effect on cor pulmonale, and it has not yet been known that the prostaglandin $I_2$ derivatives have the effect of ameriolating the condition of cor pulmonale. The inventors of this invention first found the effectiveness of the derivatives as an agent for treating cor pulmonale.

In compounds represented by the above formula (I), $R_1$ is preferably a carboxyl group or a functional derivative thereof indicated by —$COOR_7$ (wherein $R_7$ is an ester residue, specifically, methyl, ethyl or a pharmacologically acceptable cation such as an alkaline or alkaline earth metal such as sodium, potassium or calcium, an amine such as mono-, di- or trimethylamine, methyl piperidine, mono-, di- or triethanolamine, lysine, or basic amino acid); A is preferably (1) —$(CH_2)_n$—, (2) —$(CH_2)_m$—CH=CH—$(CH_2)_p$—, (3) —$(CH)_m$—C≡C—$(CH_2)$p— or (4) —$CH_2$—O—$CH_2$— (wherein n is an integer of 2 to 3, and each of m and p is 0 or 1); $R_2$ is (1) a straight chain or branched alkyl group having 5 to 7 carbon atoms, (2) —Ct H2t—$OR_3$ (wherein t indicates an integer of 1 to 3, and $R_3$ indicates a straight chain or branched alkyl group having 2 to 4 carbon atoms, or a phenyl group), (3) —Ct H2t—CH=C ($R_4$) ($R_5$) (wherein t indicates an integer of 1 to 3, and $R_4$ and $R_5$ each indicate hydrogen, a methyl group, an ethyl group, a propyl group or a butyl group); or (4) —Ct H2t—C≡C—R$_6$ (wherein t indicates an integer of 1 to 3, and R$_6$ indicates hydrogen, a methyl group or an ethyl group). Formula (I) indicates d-, l- and dl-forms. In R$_2$, —Ct H2t— represents a straight chain or branched alkylene group.

Of the above-described compounds, the following compound, beraprost, or a salt thereof is preferably used.

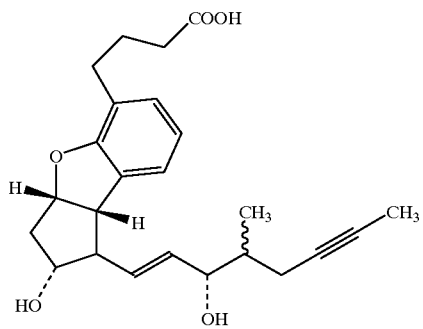

The compounds represented by formula (I) can be produced by, for example, the method disclosed in Japanese Examined Patent Publication No. 1-53672.

Oral or parenteral administration of the compounds represented by formula (I) brings about the significant curative effect on cor pulmonale.

Cor pulmonale develops a cardiac disorder secondarily caused by various pulmonary diseases and pulmonary vascular diseases in the pathophysiological state wherein hypoxemia (coexisting with hypercapnemia) resulting from pulmonary insufficiency continues, thereby causing right ventricular pressure overload (an increase in work load of the right ventricle). When this state continues, right ventricular hypertrophy and right ventricular failure arise. Cor pulmonale is classified into acute, subacute and chronic cor pulmonale. Although the compounds represented by formula (I) of the present invention are effective against acute, subacute and chronic cor pulmonale, the compounds are particularly effective against chronic cor pulmonale.

A typical causal disease of acute cor pulmonale is pulmonary embolism which causes significant dilation of the right ventricle without right ventricular hypertrophy, resulting in right ventricular failure. Although causes of subacute cor pulmonale include multiple and repetitive minor pulmonary embolism, dispersion of cancer to the lungs, and compression of the pulmonary main artery due to a tumor, etc., the condition thereof is similar to acute cor pulmonale. Chronic cor pulmonale is frequently caused by a chronic obstructive lung disease.

Examples of causal diseases of cor pulmonale include pulmonary embolism, dispersion of cancer to the lungs, pulmonary tuberculosis, compression of the pulmonary main artery due to a tumor, pulmonary infarction, diseases which cause primary disorder of the passage of air through the lungs and pulmonary alveoli (for example, chronic bronchitis, bronchial asthma, pulmonary emphysema, pulmonary fibrosis, pulmonary granulomatosis and humectation, pulmonary abscission, congenital pulmonary cyst, and height hypoxia), diseases causing primary disorder of the thoracic motion (for example, kyphosis and other thoracic deformity, pleural fibrosis, chronic nerve-muscular atrophy, obesity accompanied with alveolar hypoventilation, and cataplectic alveolar hypoventilation), diseases causing primary disorder of the pulmonary vessels (for example, primary disorder of the aterial paries, thrombotic diseases, embolism, mediastinal tumor, aneurysm, and compression of the pulmonary main artery and veins due to granulomatosis or fibrosis).

The agent for treating cor pulmonale of the present invention is used not only for treating cor pulmonale but also for preventing cor pulmonale.

The compound represented by formula (I) is administered to an adult one to three times a day in a dosage of 0.01 to 100 mg/person.

The agent for treating cor pulmonale of the present invention may comprise at least one of the compounds represented by formula (I) or salts thereof, or further contain the additives below so that the agent in a solid state can orally be administered.

Examples of such additives include excipients such as starch, lactose, sucrose, grape sugar, mannitol, calcium carbonate, calcium sulfate, and the like; binders such as starch, dextrin, gum arabic, traganth, methyl cellulose, gelatin, polyvinyl pyrrolidone, polyvinyl alcohols and the like; disintegrators such as starch, polyvinyl pyrrolidone, crystalline cellulose and the like; lubricants such as magnesium stearate, talc and the like; colorants; flavors; and the like.

The compounds represented by formula (I) used in the present invention can be used in various conventional dosage forms such as tablets, sugar-coated tablets, powders. granules, troches, capsules, pills, syrup, and the like. The compounds may be parenterally administered in the form of a sterilized solution, and other solutes such as sodium chloride or glucose in an amount sufficient to prepare an isotonic solution can also be used. Since the agent for treating cor pulmonale of the present invention has the stable chemical structure, it has no difficult in preparation and can be administered in the foregoing dosage forms for oral administration and a wide verity of other dosage forms such as an injection, a suppository, etc.

EXAMPLE

Although it will be described with reference to the following compound 1 beraprost sodium (referred to as "BPS" hereinafter) as an example that the compounds represented by formula (I) have the effect of treating cor pulmonale, the compounds are not limited to this.

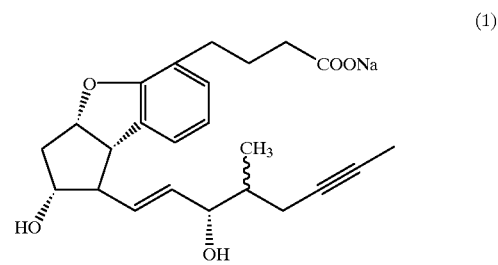

(1)

Example 1

Model Test of Monocrotalin-Induced Disease

Monocrotalin was subcutaneously administered to 7-week-old SD male rats, and, 7 days after the administration, compound 1 was then continuously orally administered to the rats for 14 days to examine the effect of treating cor pulmonale. Compound 1 was used as a test compound. After the completion of the test, the rats were killed, and the weight ratio of the right ventricle of the heat, {weight of the right ventricle/(weight of the left ventricle+weight of the septum)×100(%)}, was determined.

BPS's Action on Weight Ratio (%) of Right Ventricle/[Left Ventricle+Septum] of Monocrotalin-administered Rats

|  | mean ± S.E.M. |
| --- | --- |
| Normal | 26.8 ± 1.1** |
| Control | 50.0 ± 2.9 |
| BPS 0.01 mg/kg | 42.9 ± 2.7 |
| BPS 0.03 mg/kg | 36.1 ± 2.6** |
| BPS 0.1 mg/kg | 38.9 ± 3.3* |

Statistical significant difference: *$p < 0.05$, **$p < 0.01$ vs. control

It was confirmed that compound 1 significantly depress an increase in the weight ratio of the right ventricle induced by monocrotalin, and thus has the effect of treating cor pulmonale.

Example 2

Model Test of Interleukin-6-Induced Disease

Interleukin 6 was subcutaneously administered to 7-week-old SD male rats for 6 days, and, 2 days after the administration, compound 1 was then continuously orally administered to the rats for 5 days to examine the effect of curing cor pulmonale. Compound 1 was used as a test compound. After the completion of the test, the rats were killed, and the weight ratio of the right ventricle of the heat, {weight of the right ventricle/(weight of the left ventricle+weight of the septum)×100(%)}, was determined.

BPS's Action on Weight Ratio (%) of Right Ventricle/[Left Ventricle+Septum] of IL-6-administered Rats

|  | mean ± S.E.M. |
| --- | --- |
| Normal | 26.1 ± 0.9** |
| Control | 32.2 ± 0.7 |
| BPS 0.01 mg/kg | 30.1 ± 1.0 |
| BPS 0.1 mg/kg | 29.6 ± 1.0* |

Statistical significant difference: *$p < 0.05$, **$p < 0.01$ vs. control

It was confirmed that compound 1 significantly depress an increase in the weight ratio of the right ventricle induced by interleukin 6, and thus has the effect of treating cor pulmonale.

Example 3

Pulmonary Embolism Model Test

Collagen (5 μg/head) and epinephrine (0.6 μg/head) were simultaneously injected into the caudal veins of 7-week-old ddY male mice (27–30 g) obtained from Nippon S.L.C. Co., Ltd. to cause pulmonary embolism. One week after pulmonary embolism was induced, the wet weight/dry weight ratio of the lungs and the weight ratio of the right ventricle, {weight of the right ventricle/(weight of the left ventricle+weight of the septum)×100(%)}, were determined. Compound 1 (0.01 mg/kg, 0.03 mg/kg, 0.1 mg/kg) was orally administered every day for 7 days from the day after inducing pulmonary embolism.

BPS's action on the wet weight/dry weight ratio of the lungs and the weight ratio of the right ventricle of pulmonary embolism model mice simultaneously administered with collagen and epinephrine.

|  | Wet weight/dry weight ratio of lungs mean ± S.E.M. | Weight ratio of right ventricle mean ± S.E.M. | n |
| --- | --- | --- | --- |
| Normal | 3.84 ± 0.01* | 28.2 ± 0.9** | 5 |
| Control | 3.96 ± 0.04 | 32.3 ± 0.9 | 8 |
| BPS 0.01 mg/kg | 3.92 ± 0.04 | 30.1 ± 1.4 | 6 |
| BPS 0.03 mg/kg | 3.85 ± 0.02* | 27.8 ± 1.4 | 6 |
| BPS 0.1 mg/kg | 3.85 ± 0.02* | 27.3 ± 1.1** | 6 |

Statistical significant difference: *$p < 0.05$, **$p < 0.01$ vs. control

Compound 1 significantly depressed the wet weight/dry weight ratio of the lungs and exhibited the effect of inhibiting pulmonary embolism. Compound 1 further significantly depressed the weight ratio of the right ventricle and was thus confirmed to have the effect of treating cor pulmonale.

INDUSTRIAL APPLICABILITY

The agent of treating cor pulmonale of the present invention exhibits excellent pharmaceutical effects in both oral and parenteral administration.

What is claimed is:

1. A method of treating cor pulmonale comprising administering to a patient of cor pulmonale an effective amount of a 5,6,7-trinor-4,8-inter-m-phenyleneprostaglandin $I_2$ derivative or a pharmacologically acceptable salt thereof represented by the following formula (I):

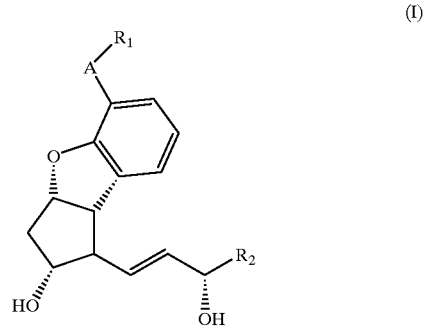

wherein $R_1$ is hydrogen, —$COOR_7$, (wherein $R_7$ is an ester group, or a pharmacologically acceptable cation), —$CH_2OH$, or a pharmacologically acceptable cation;

A is —(CH₂)n—, —(CH₂)m—CH=CH—(CH₂)p—, —(CH)m—C≡C—(CH₂)p— or —CH₂—O—CH₂— (wherein n is an integer of 0 to 3, and each of m and p is 0 or 1), R₂ is (1) a straight chain or branched alkyl group having 5 to 10 carbon atoms, (2) —C$_t$H2$_t$—OR₃ (wherein t indicates an integer of 1 to 5, and R₃ indicates a straight chain or branched alkyl group having 1 to 5 carbon atoms, or a phenyl group), (3) —C$_t$H2$_t$—CH=C(R₄)(R₅) (wherein t indicates the same as defined above, and R₄ and R₅ each indicate hydrogen, a methyl group, an ethyl group, a propyl group or a butyl group); or (4) —C$_t$H2$_t$—C≡C—R₆ (wherein t indicates the same as defined above, and R₆ indicates hydrogen, a methyl group or an ethyl group); and formula (I) indicates d-, l- and dl-forms.

2. The method of treating cor pulmonale according to claim 1, wherein the compound represented by formula (I) is:

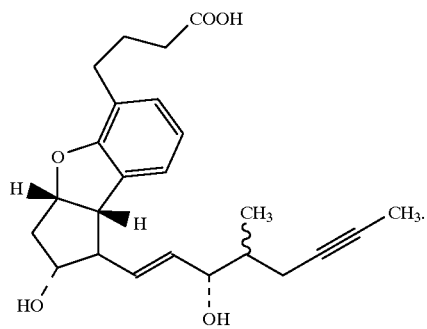

3. The method of treating cor pulmonale according to claim 1, wherein cor pulmonale is acute, subacute or chronic cor pulmonale.

4. The method of treating cor pulmonale according to claim 1, wherein cor pulmonale is chronic cor pulmonale.

* * * * *